United States Patent
Kruss et al.

(10) Patent No.: US 6,828,311 B2
(45) Date of Patent: Dec. 7, 2004

(54) FORMULATION FOR THE PARENTERAL APPLICATION OF A SODIUM CHANNEL BLOCKER

(75) Inventors: Bernd Kruss, Hochdorf (DE); Annerose Mauz, Langenenslingen-Emerfeld (DE); Karin Ruehr, Biberach (DE); Jean Marie Stassen, Lubbeek (BE); Claus Veit, Biberach (DE); Klaus Wagner, Warthausen (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 43 days.

(21) Appl. No.: 10/446,611

(22) Filed: May 28, 2003

(65) Prior Publication Data

US 2004/0019013 A1 Jan. 29, 2004

Related U.S. Application Data

(60) Provisional application No. 60/395,836, filed on Jul. 15, 2002.

(30) Foreign Application Priority Data

May 29, 2002 (DE) .......................................... 102 23 783

(51) Int. Cl.$^7$ ..................... A61K 31/724; A61K 31/485
(52) U.S. Cl. ......................................... 514/58; 514/295
(58) Field of Search .................................. 514/58, 295

(56) References Cited

U.S. PATENT DOCUMENTS 6,455,538 B1  9/2002  Grauert et al.

FOREIGN PATENT DOCUMENTS

| EP | 0 197 571 A2 | 3/1985 |
|---|---|---|
| WO | WO 95/06485 | 3/1995 |
| WO | WO 95/17191 | 6/1995 |
| WO | WO 99/14199 | 3/1999 |

OTHER PUBLICATIONS

Adrian J. Carter, et al., "Potent Blockade of sodium channels and protection of brain tissue from ischemia by Bill 890 CL", PNAS, Apr. 25, 2000, vol. 97, No. 9 pp 4944–4949.

Bernd Kruss "New Formulation for the Parenteral Application of Crobenetine" U.S. Appl. No. 10/446,613 filed May 28, 2003.

Charles P. Taylor, et al. "Na+ Channels as Targets for Neuroprotective Drugs" Trends in Pharmacological Sciences, Elsevier Trends Journal, Cambridge, GB vol. 16, Sep. 1995 pp. 309–316 (1995).

Thorsten Anger, et al. "Medicinal Chemistry of Neuronal Voltage–Gated Sodium Channel Blockers" Journal of Medicinal Chemistry, vol. 44, No. 2 Jan. 2001, pp. 115–137 (2001).

Primary Examiner—James O. Wilson
Assistant Examiner—Leigh C. Maier
(74) Attorney, Agent, or Firm—Robert P. Raymond; Michael Morris; David A. Dow

(57) ABSTRACT

The invention relates to a new formulation containing Bill 890 or one of the pharmaceutically acceptable salts thereof for parenteral administration.

29 Claims, No Drawings

FORMULATION FOR THE PARENTERAL APPLICATION OF A SODIUM CHANNEL BLOCKER

RELATED APPLICATIONS

Benefit of U.S. Provisional Application Ser. No. 60/395,836, filed on Jul. 15, 2002 is hereby claimed, and said Application is herein incorporated by reference.

The invention relates to a new formulation of (−)-(1R,2″S)-2-(2″-benzyloxy)propyl-4′-hydroxy-5,9,9-trimethyl-6,7-benzomorphan (Bill 890) or one of the pharmacologically acceptable salts thereof, particularly the hydrochloride thereof, containing a complex of the active substance and a cyclodextrin, particularly hydroxypropyl-γ-cyclodextrin, optionally in the presence of a hydroxy acid, for parenteral, particularly intravenous administration, the preparation and use thereof.

The terms "Bill 890" and "active substance" always refer to the compound (−)- (1R,2″S)-2-(2″-benzyloxy)propyl-4′-hydroxy-5,9,9-trimethyl-6,7-benzomorphan of formula

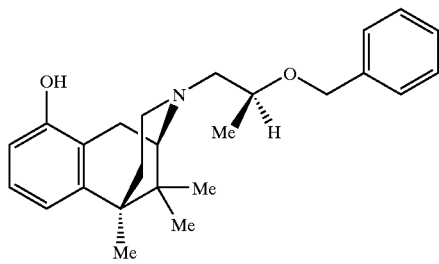

known from WO 99/14199, in the form of the free base or the corresponding acid addition salts with pharmacologically acceptable acids, particularly in the form of the hydrochloride. Other names for Bill 890 are crobenetine and [2R-[2,3(S*),6]]-1,2,3,4,5,6-hexahydro-6, 11,11-trimethyl-3-[2-(phenylmethoxy)propyl]-2,6-methano 3-benzazocin-10-ol. Bill 890 is a sodium channel blocker with neuroprotective properties; the main indications for its use are thromboembolic stroke, brain injury and pain.

The aim of the invention is to prepare a new formulation for the active substance Bill 890, particularly for the hydrochloride thereof.

The invention relates to pharmaceutical compositions containing the active substance Bill 890 or one of the pharmaceutically acceptable salts thereof, particularly the hydrochloride thereof, and a cyclodextrin derivative, particularly gamma-cyclodextrin (γ-CD), hydroxypropyl-gamma-cyclodextrin (HP-γ-CD), hydroxypropyl-beta-cyclodextrin (HP-β-CD) or sulphobutylether-beta-cyclodextrin (SBE-β-CD). The preferred cyclodextrin derivative is hydroxypropyl-γ-cyclodextrin. Hydroxypropyl-γ-cyclodextrin with a molar substitution rate of 0.5 to 0.7 is sold for example by Messrs Wacker-Chemie GmbH, D-Burghausen, under the name "CAVASOL® W8 HP Pharma". "CAVASOL® W8 HP Pharma" is particularly preferred for the pharmaceutical composition according to the invention.

For the indications mentioned above dosage is easily controlled so as to ensure that steady-state plasma levels are safely maintained. Bill 890 is therefore conveniently administered by parenteral route.

Apart from the active substance and the cyclodextrin derivative the pharmaceutical compositions according to the invention intended for parenteral administration may contain hydroxy acids such as for example malic acid, lactic acid, tartaric acid or citric acid. They may optionally also contain conventional excipients and carriers such as for example the isotonic agents glucose, mannitol or sodium chloride or sodium acetate or sodium acetate trihydrate as a buffer combined with acetic acid or a citric acid/phosphate buffer consisting e.g. of citric acid and disodium hydrogen phosphate or disodium hydrogen phosphate-dihydrate. The solvent used is normally water for injections.

The individual embodiments of the invention will be explained in more detail hereinafter.

Complexing the active substance with cyclodextrins

Suitable cyclodextrins include for example substituted β-cyclodextrin (consisting of 7 glucopyranose units), hydroxypropyl-β-cyclodextrin (HPβCD), sulphobutylether-β-cyclodextrin (SBEβCD), γ-cyclodextrin (consisting of 8 glucopyranose units) and hydroxypropyl-γ-cyclodextrin (HPγCD).

Solubility experiments and $^1$H-NMR spectra have surprisingly shown that γ-cyclodextrin as well as hydroxypropyl-γ-cyclodextrin (HPγCD), hydroxypropyl-βcyclodextrin (HPβCD) and sulphobutylether-β-cyclodextrin (SBEβCD) complex the hydrochloride of Bill 890.

Complexing the active substance with cyclodextrins and hydroxy acids

Another embodiment of the invention relates to the complexing of the active substance or one of the salts thereof with cyclodextrins and hydroxy acids. The amount of cyclodextrin required can be reduced by the formation of a ternary complex consisting of Bill 890, the cyclodextrin in question and a hydroxy acid. The suitable cyclodextrins include, for example, hydroxypropyl-β-cyclodextrin (HPβCD), sulphobutylether-β-cyclodextrin (SBEβCD), γ-cyclodextrin and hydroxy-propyl-γ-cyclodextrin (HPγCD). Suitable hydroxy acids include for example malic acid, lactic acid, tartaric acid and citric acid.

One embodiment according to the invention of a parenteral preparation of Bill 890 or one of the physiologically acceptable salts thereof, such as e.g. the hydrochloride, contains the active substance in doses of 1 mg/kg of body weight to 30 mg/kg of body weight per day, preferably in the range from 3–15 mg/kg of body weight. The amounts, concentrations and dosages specified relate in each case to the active substance base regardless of whether Bill 890 is used in the form of the "bases" (=compound of the formula given on page 1) or in the form of one of the pharmacologically acceptable salts thereof.

The preparation is preferably administered by continuous infusion over 24 hours or optionally several days in order to maintain a steady-state plasma level. The volumes administered are in the range from 50 to 500 ml, preferably 100 to 250 ml, i.e. the concentrations for administration of the active substance are in the range from 150 mg/500 ml=0.3 mg/ml (0.03%) to 1500 mg/100 ml=15 mg/ml (1.5%). An active substance concentration of 0.5 mg/ml=0.05% (g/v) to 3.5 mg/ml=0.35% (g/v) is preferred.

The molar ratio of active substance to cyclodextrin is between 1:1 and 1:5 according to the invention. A molar ratio of 1:2.5 to 1:3.5 is preferred. In the presence of hydroxy acid the molar ratio of active substance to cyclodextrin is between 1:0.5 and 1:3 according to the invention; a molar ratio of 1:0.5 to 1:1.5 is preferred.

The following Examples are intended to illustrate the invention in more detail:

EXAMPLES

Example 1

Solution for infusions/injection containing a hydroxypropyl-γ-cyclodextrin complex

| | |
|---|---|
| BIII 890 hydrochloride | 767 mg* |
| HpγCD** | 10000 mg |
| mannitol | 11000 mg |
| acetic acid 99% | 125.25 mg |
| sodium acetate trihydrate | 56.5 mg |
| water for injections ad | 250 ml |

*corresponds to 700 mg BIII 890 in the form of the base
**for example "CAVASOL ® W8 HP Pharma" sold by Wacker

Example 2

Solution for infusion/injection containing a γ-cyclodextrin complex

| | |
|---|---|
| BIII 890 CL | 383.5 mg*** |
| γCD | 5000 mg |
| NaCl | 2250 mg |
| water for injections ad | 250 ml |

***corresponds to 350 mg BIII 890 in the form of the base

Example 3

Solution for infusion/injection containing a hydroxypropyl-β-cyclodextrin complex

| | |
|---|---|
| BIII 890 CL | 767 mg* |
| HPβCD | 7500 mg |
| mannitol | 12500 mg |
| acetic acid 99% | 125.25 mg |
| sodium acetate trihydrate | 56.5 mg |
| water for injections ad | 250 ml |

*corresponds to 700 mg BIII 890 in the form of the base

Example 4

Solution for infusion/injection containing a sulphobutylether-β-cyclodextrin complex

| | |
|---|---|
| BIII 890 CL | 767 mg* |
| SBEβCD | 5000 mg |
| mannitol | 12500 mg |
| acetic acid 99% | 125.25 mg |
| sodium acetate trihydrate | 56.5 mg |
| water for injections ad | 250 ml |

*corresponds to 700 mg BIII 890 in the form of the base

Example 5

Solution for infusion/injection containing a hydroxypropyl-γ-cyclodextrin complex in the presence of hydroxy acids

| | |
|---|---|
| BIII 890 CL | 767 mg* |
| HPγCD | 2500 mg |
| citric acid | 708 mg |
| mannitol | 12500 mg |
| acetic acid 99% | 125.25 mg |
| sodium acetate trihydrate | 56.5 mg |
| water for injections ad | 250 ml |

*corresponds to 700 mg BIII 890 in the form of the base

Example 6

Solution for infusion/injection containing a γ-cyclodextrin complex in the presence of a hydroxy acid

| | |
|---|---|
| BIII 890 CL | 767 mg* |
| γCD | 2500 mg |
| tartaric acid | 138.25 mg |
| NaCl | 2250 mg |
| water for injections ad | 250 ml |

*corresponds to 700 mg BIII 890 in the form of the base

The quantity of active substance administered can be controlled by the administration of a specific volume of one of the solutions described above. For example the daily administration of 100 ml of a solution according to Example 1 corresponds to the administration of 280 mg of Bill 890 per day.

We claim:

1. Pharmaceutical composition comprised of a cyclodextrin complex of Bill 890 or a pharmacologically acceptable salt thereof.

2. Pharmaceutical composition comprised of a ternary complex consisting of Bill 890 or a pharmacologically acceptable salt thereof, a cyclodextrin and a hydroxy acid.

3. Pharmaceutical composition according to claim 2 containing the hydrochloride of Bill 890, HP-γ-CD and citric acid.

4. Pharmaceutical composition according to claim 2, wherein said hydroxy acid is selected from the group consisting of malic acid, lactic acid, tartaric acid and citric acid.

5. Pharmaceutical composition according to claim 4, wherein the hydroxy acid is a citric acid.

6. Pharmaceutical composition comprised of Bill 890 or one of the pharmacologically acceptable salts thereof in combination with a substituted or unsubstituted cyclodextrin.

7. Pharmaceutical composition according to claim 6 containing the hydrochloride of Bill 890 and HP-γ-CD.

8. Pharmaceutical composition according to claim 1, wherein the cyclodextrin is selected from the group consisting of γ-CD, HP-γ-CD, HP-β-CD and SBE-β-CD.

9. Pharmaceutical composition according to claim 8, wherein HP-γ-CD is used as the cyclodextrin.

10. Pharmaceutical composition according to claim 1, wherein the hydrochloride of Bill 890 is used.

11. Pharmaceutical composition according to claim 1 for parenteral administration.

12. Pharmaceutical composition according to claim 1, wherein the concentration of Bill 890 is between 0.3 mg/ml and 15 mg/ml.

13. Pharmaceutical composition according to claim 12, wherein the concentration of Bill 890 is between 0.5 mg/ml and 3.5 mg/ml.

14. Pharmaceutical composition according to claim 1, wherein the molar ratio of Bill 890 to cyclodextrin is between 1:1 and 1:5.

15. A complex of Bill 890 or one of the pharmacologically acceptable salts thereof with a cyclodextrin as complexing agent.

16. A complex according to claim 15, wherein the cyclodextrin is selected from the group consisting of γ-CD, HP-γ-CD, HP-β-CD and SBE-β-CD.

17. A complex of claim 15, wherein the cyclodextrin is hydroxypropyl-γ-cylcodextrin.

18. A method of treating stroke in a patient needing such treatment by administering a therapeutically effective amount of a pharmaceutical composition comprised of Bill 890 or one of the pharmacologically acceptable salts thereof and a) a cyclodextrin complex or b) a cyclodextrin complex in the presence of a hydroxy acid.

19. Method of treating stroke by administering to a patient in need thereof a therapeutically effective amount of a pharmaceutical composition comprised of Bill 890 or one of the pharmacologically acceptable salts thereof and cyclodextrin.

20. The method of claim 19, wherein the cyclodextrin is a substituted γ-cyclodextrin.

21. The method of claim 20, wherein the γ-cyclodextrin is HP-γ-CD.

22. The method of claim 19, wherein the pharmaceutical composition is administered intravenously.

23. The method of claim 19, wherein the pharmaceutical composition is further comprised of an hydroxy acid.

24. The method of claim 23, wherein the hydroxy acid is malic acid, lactic acid, tartaric acid or citric acid.

25. The method of claim 24, wherein the hydroxy acid is a tartaric acid or malic add.

26. Method according to claim 19, wherein the concentration of Bill 890 is between 0.3 mg/ml and 15 mg/ml.

27. Method according to claim 26, wherein the concentration of Bill 890 is between 0.5 mg/ml and 3.5 mg/ml.

28. Method according to claim 19, wherein the molar ratio of Bill 890 to cyclodextrin is between 1:1 and 1:5.

29. Method according to claim 19, for the treatment of acute stroke.

\* \* \* \* \*